United States Patent [19]

Chaffin

[11] Patent Number: Plant 6,844

[45] Date of Patent: Jun. 13, 1989

[54] MINIATURE ROSE PLANT 'HONEY BEAR'

[76] Inventor: Lauren M. Chaffin, 4121 Prospect Ave., Yorba Linda, Calif. 92686

[21] Appl. No.: 177,582

[22] Filed: Apr. 4, 1988

[51] Int. Cl.[4] ..... A01H 5/00

[52] U.S. Cl. ..... Plt./7

[58] Field of Search ..... Plt./7

*Primary Examiner*—James R. Feyrer

[57] ABSTRACT

The subject of the present disclosure is a new and distinct variety of miniature rose plant characterized by light apricot blend buds and flowers of distinctive form and further identified by the rounded, dwarf, compact plant.

1 Drawing Sheet

1

The present invention relates to a new and distinct variety of hardy, dwarf, bush type rose plant of the miniature class; the variety being primarily characterized —as to novelty—by the light apricot blend buds and flowers which in general coloring effect are similar to Colibri (Miniature—non-patented).

The variety is further characterized by:

An abundance of bloom, with flowers borne one to a stem with rarely a side bud. Slightly fragrant.

A plant which is vigorous, of rounded, bushy growth habit, semi-glossy foliage with broad pointed leaflets; the buds and flowers being similar in form and size to Rise 'N Shine its seed parent (Miniature—U.S. Plant Pat. No. 4,231).

The plant which has a normal height of 10 to 12 inches, can easily be maintained by occasional trimming.

A plant which grows and blooms satisfactorily both in a greenhouse or outdoors; is good for growing in pots; and provides excellent garden decoration as well as cut flowers.

The present variety of miniature rose was originated by me at my nursery (Pixie Treasures Miniature Rose Nursery, 4121 Prospect Ave. Yorba Linda, Orange County, Calif.) under conditions of careful control and observation, as a cross between Rise 'N Shine (Miniature—U.S. Plant Pat. No. 4,231) as the seed parent and Holy Toledo (Miniature—U.S. Plant Pat. No. 4,659) as the pollen parent.

Subsequent to origination of the variety I successfully asexually reproduced it at the nursery, located as foresaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color identification are employed.

Type: Hardy; bushy; dwarf; rounded; upright; seedling; greenhouse; outdoors; cut flowers; garden decoration; pot plant.

Class: Miniature.

*Market name.*—Honey Bear.

*International identifier.*—Pixihon.

2

Flowers borne: Singly on slightly curved, slender stems; rarely a side-bud.

Quantity of bloom: Abundant all season, outdoors and in greenhouse.

Bud:

*Peduncle.*—Medium length, 2½–3 cm; erect; slender; slightly curved; sturdy; lt. green tinted bronze; few glands; few hairs.

*Size.*—Before calyx breaks — 2–2½ cm.

*Form.*—Pointed; foliaceous parts extend beyond tip of bud one quarter or more of its length.

*Color.*—Medium green. As calyx breaks — surface of outside petal showing color near to Orpiment orange 10/2.

Bloom:

*Size.*—When fully open — small, averaging 1¾ to 2 in. or 5 cm measuring across top of bloom.

*Petalage.*—Very double, 40 to 45 petals, arranged symmetrically.

*Form.*—From urn shaped bud it opens informally with outer petals curving downward at sides; inside petals which are not as broad curve downward only slightly.

Petals:

*Substance.*—Moderately thick and of good substance.

*Texture.*—Smooth and satiny on both surfaces. Slightly veined.

*Shape.*—Outside petal: Smooth edged. Broad with definite point at apex. Broad base. Width — approximately 2 to 2½ cm. Intermediate petal: Same as outside petal — varying in width from 1¼ to 1½ cm. Inside petal: Same as outside and intermediate petal but smaller with few petaloids close to stamens.

Color: One half to three quarters open flowers from plants grown outdoors at Pixie Treasures Rose Nursery, Yorba Linda, Calif., March 1988.

*Outside petal.*—Outside surface: Outer edge and center area near in coloring to Cadmium orange 8/3 blending to base of a hue close to Indian yellow 6/2. Inside surface: Outer edge and center area near in coloring to Tangerine orange 9/3 blending to base of a hue close to Indian yellow 6/2.

*Intermediate petal.*—Outside surface: Outer edge and center area near in coloring to Indian yellow 6/3 blending deeper to near Indian yellow 6/2 at the base. Inside surface: Same as inside surface of outside petal. Base same.

*Inside petal.*—Same as intermediate petal. Same base.

General coloring effect:

*Newly open flowers.*—Symetrically arranged petals of the lighter shades of Tangerine and Cadmium orange with a darker hue of the same coloring on the inner petals.

*Three days open.*—Keeps symmetry when fully open with no stamens showing. Holds delicate coloring well. Outer edges of outside petals sometimes bears a tinge of light pink from exposure.

Behavior: Opens well in all weather. Petals tend to hang on for 5 to 6 days, then fall clean, calyx remains and occasionally forms a hip.

*Flower longivity* (*March* 1988).—Plant in pot — 4 to 5 days; plant in ground — 5 to 6 days; cut flowers at living room temperature — 3 to 4 days.

Reproductive organs:

*Stamens.*—45 to 50; flairing outward.

*Filiments.*—2 to 4 mm; uneven lengths.

*Anthers.*—Light golden; introse.

*Pollen.*—Moderate amount.

*Pistils.*—Projects above disc.

*Styles.*—25 to 30; loosely flairing; 4 to 5 mm; light mauve.

*Ovaries.*—Enclosed in calyx.

*Hips.*—Few if any.

*Sepals.*—Spear shaped; reflexed.

*Seeds.*—Few if any.

Foliage:

*Leaves.*—Compound of five leaflets; length — varying 2 to 2½ in. or 5 to 6½ cm; semi-glossy; good substance.

*Leaflets.*—Broad lanceolate and ⅔ rds. as wide as its length; supported by a very short petiolule.

*Rachis.*—Length 3½ to 4 cm; upper side grooved; underside — 2 or 3 soft thorns.

*Stipules.*—Medium long, smooth; auricles flairing outward at 45 degrees.

*Color.*—Medium green; rachis — bronze; serrated edges — green.

Growth:

*Habit.*—Dwarf; upright and rounded; height — 25 to 30 cm or 10 to 12 inches.

*Growth.*—Moderately vigorous; 2 to 3 cm between internodes.

*Canes.*—Slender; sturdy.

*Main stems.*—Medium green.

*Branches.*—Much branched; medium green.

*Thorns.*—Moderate amount; small, dilated at base.

*New shoots.*—Green — bronze edged.

The following is claimed:

1. A new and distinct variety of miniature rose plant of hardy, dwarf, bushy, upright, rounded, much branched habit substantially as illustrated and described, characterized by buds and flowers which are in a color hue similar to Colibri (Miniature rose—non patented) giving a coloring effect of light apricot blend and resembling Rise 'N Shine (Miniature rose—U.S. Plant Pat. No. 4,231) in form and size; having buds and flowers of a distinctive and unusual appearance as compared to other miniature rose plants; said flowers being fully double, uniquely formed and further characterized by a compact growth habit with abundant foliage, ease of propagation from soft-wood cuttings or by budding, and being a prolific producer of flowers.

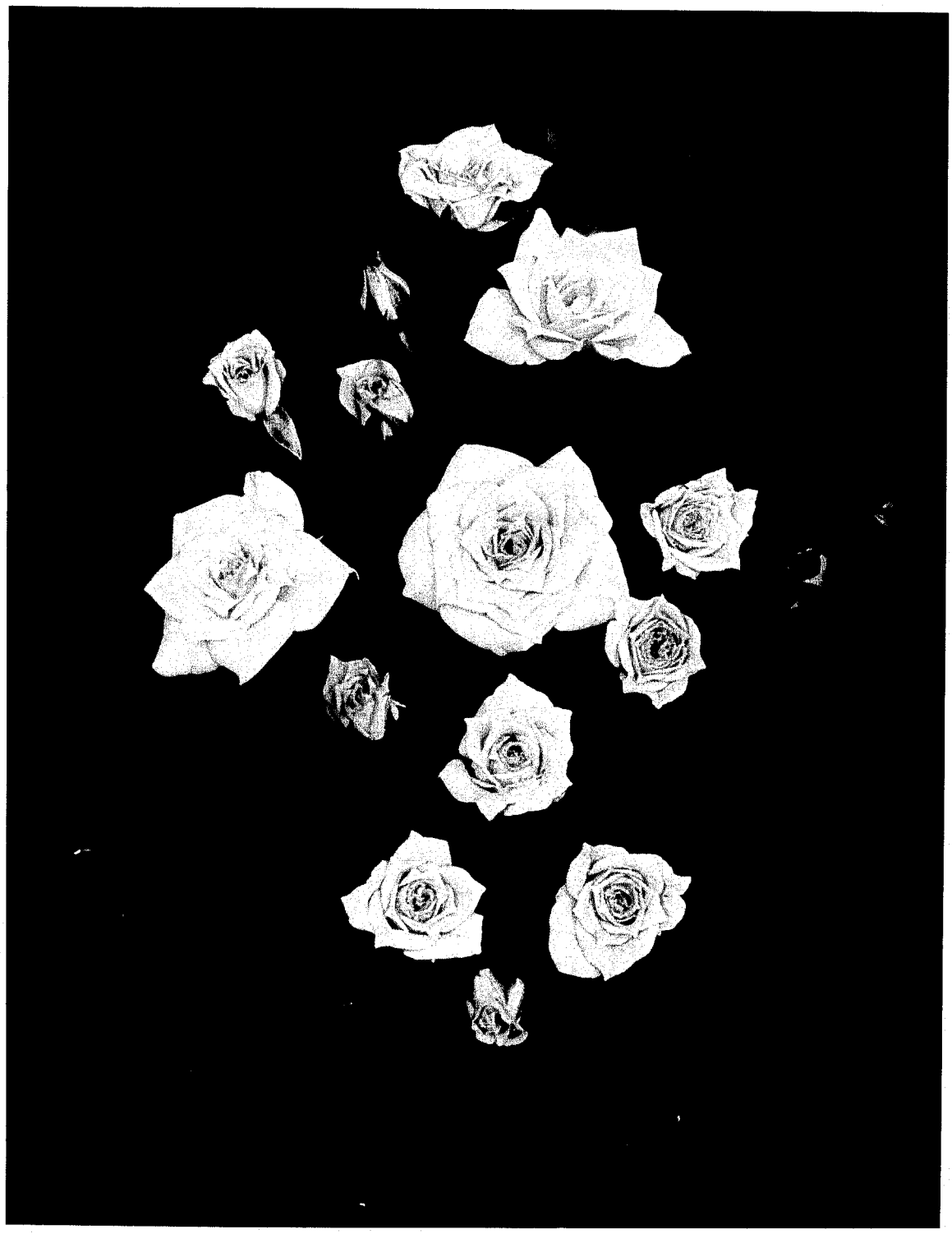

* * * * *